United States Patent [19]

Martin

[11] Patent Number: 5,126,445

[45] Date of Patent: Jun. 30, 1992

[54] PROCESS FOR THE PREPARATION OF CEFODIZIME SODIUM

[75] Inventor: Wolfgang Martin, Kelkheim, Fed. Rep. of Germany

[73] Assignee: Hoechst Aktiengesellschaft, Frankfurt am Main, Fed. Rep. of Germany

[21] Appl. No.: 506,920

[22] Filed: Apr. 5, 1990

[30] Foreign Application Priority Data

Apr. 7, 1989 [DE] Fed. Rep. of Germany ....... 3911322

[51] Int. Cl.⁵ ............................................ C07D 501/36
[52] U.S. Cl. ..................................... 540/227; 540/226
[58] Field of Search ........................ 540/227, 222, 221

[56] References Cited

U.S. PATENT DOCUMENTS 4,590,267 5/1986 Scheunemann et al. ............. 544/27
4,912,211 3/1990 Bonfanti ............................. 540/227

FOREIGN PATENT DOCUMENTS

78532-B1 1/1987 European Pat. Off. .

Primary Examiner—Nicholas S. Rizzo
Attorney, Agent, or Firm—Finnegan, Henderson, Farabow, Garrett and Dunner

[57] ABSTRACT

A process for the preparation of cefodizime sodium, which comprises bringing cefodizime into solution in ethanol having a water content of 4–15% by means of 1.5–2.5 moles of an organic amine base and allowing the disodium salt of the cefodizime to crystallize by adding a sodium donor.

9 Claims, No Drawings

PROCESS FOR THE PREPARATION OF CEFODIZIME SODIUM

According to EP-PS 78,532, crystalline cefodizime sodium is prepared by dissolving cefodizime in water by means of sodium bicarbonate and subsequent crystallization by addition of ethanol or isopropanol.

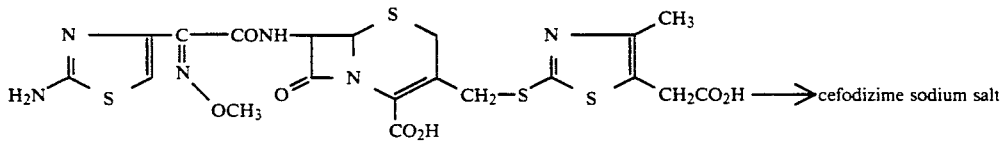

Under practical conditions, a water-ethanol (2:1) mixture is used (3 parts), with the addition of 10% strength aqueous sodium hydroxide solution (1.2 parts), so that the water content of the cefodizime sodium solution initially prepared is about 50%. After sterile filtration, cefodizime sodium is precipitated using about 20 parts of ethanol. Based on the water content of about 50% in the solution, corresponding losses occur solely on the basis of the solubility of the product in water. The water content also necessitates a correspondingly large amount of ethanol for precipitation, from which a poor volume utilization also results. In addition, the process has to be carried out temporarily using a supersaturated solution, with the risk of uncontrolled crystallization. Furthermore, at least 1-2 hours are required for dissolving by means of 2.5N sodium hydroxide solution. Certain damage to the product due to local overalkalization by sodium hydroxide solution and due to the long dissolving time is not to be excluded in this process.

It has now been found that cefodizime sodium can be prepared substantially more easily, gently and economically and with a substantially higher yield (above 85% of theory, instead of about 60%), by bringing cefodizime acid into solution in ethanol, it being necessary for the ethanol to have a water content of about 4-15%, preferably 5-6%, by adding 1.5-2.5 moles, preferably 1.8-2.2 moles, in particular 2 moles, of an organic amine base, preferably triethylamine, in a gentle manner and, which is of importance for efficient production, virtually instantaneously and allowing the disodium salt of cefodizime to crystallize by adding a sodium donor.

A suitable sodium donor is preferably sodium 2-ethylhexanoate.

The dissolving procedure is expediently carried out with slight cooling of the reaction solution to about 5°-10° C. Below 0° C., dissolution is made more difficult.

Surprisingly, small amounts of water (about 4-15%, preferably about 5-6% of the total mixture) are very essential for this dissolving procedure. Without this addition of water, thick, non-filterable are obtained on attempting to dissolve cefodizime acid in the water-miscible alcohols ethanol, isopropanol and n-propanol or in acetone. Only a small addition of water causes smooth dissolution.

In the preferred embodiment of the process according to the invention using ethanol, a predominantly ethanolic solution is obtained with the aid of comparably small amounts of water (proportion of the total mixture preferably about 5-6%), which can be sterile-filtered without problems without the fear of premature crystallization of the sodium salt, particularly under working conditions.

Cefodizime sodium is crystallized from the solution, if appropriate clarified using carbon and (steriles) filtered, by the addition of 2 mole equivalents of a suitable sodium donor, preferably sodium 2-ethylhexanoate, also dissolved in ethanol. An excess of about 10-15% is expediently used. After adding about a third of the theoretically required amount of reagent, the precipitation of the cefodizime disodium salt in crystalline form begins. It can be promoted by seeding. The crystallization is carried out at about 5°-20° C. The temperature increases from about 10 to about 20° C. during the addition of sodium 2-ethylhexanoate. The crystal suspension is stirred for about 1 hour more at room temperature, and the crystals are filtered off with suction, washed with ethanol and dried in vacuo at 40° C.

The essential advantages of the process lie in the higher yield (over 85% of theory, compared to about 60% by the previous process), in the considerably higher (doubled) volume utilization, in the substantially simplified and greatly shortened dissolving time, and thus the absence of possible damage to the products, in the absence of an uncontrolled crystallization, and in somewhat more favorable product properties, such as the lack of a tendency to become electrostatically charged.

It was not to be foreseen that the very simple process according to the invention would lead to the advantages mentioned above.

EXAMPLE 1

18 ml of triethylamine are added at 7°-10° C. with cooling under a blanket of nitrogen in the course of 5 minutes to 35.04 g of cefodizime acid (95%; water content 2.1%) in 250 ml of ethanol. 15 ml of water are then added dropwise at 7°-10° C. in the course of 1-2 minutes with good cooling.

1.0 g of SX II carbon is added, the mixture is stirred for 10 minutes at about 5° C., filtered and a filtered solution of 20.3 g of sodium 2-ethylhexanoate and 2 ml of 2-ethylhexanoic acid in 90 ml of ethanol are added dropwise at about 10° C. to room temperature (about 20° C.) in the course of 1 (−2) hours.

After addition of 20-30 ml of the sodium 2-ethylhexanoate solution, the mixture is repeatedly seeded. After the addition of the sodium 2-ethylhexanoate, the resulting suspension is stirred for a further 1.5-2 hours at room temperature (about 20° C.). The precipitate is filtered off with suction, washed with 200 ml of ethanol and dried, first at room temperature, then to constant weight at 45° C. in vacuo.

Yield: 32.3 g (85% of theory)

I claim:

1. A process for the preparation of cefodizime sodium, which comprises:
   (1) preparing a solution of cefodizime by adding 1.5-2.5 moles of an organic amine base to a mixture of a cefodizime acid in ethanol, wherein said ethanol has a water content of 4–15%; and (2) adding a sodium donor to said solution to bring about the crystallization of the disodium salt of cefodizime.

2. The process according to claim 1, wherein said water content is 5–6%.

3. The process according to claim 1, wherein said organic amine base is triethylamine.

4. The process according to claim 2, wherein said organic amine base is triethylamine.

5. The process according to claim 1, wherein said sodium donor is sodium 2-ethylhexanoate.

6. The process according to claim 2, wherein said sodium donor is sodium 2-ethylhexanoate.

7. The process according to claim 3, wherein said sodium donor is sodium 2-ethylhexanoate.

8. The process according to claim 4, wherein said sodium donor is sodium 2-ethylhexanoate.

9. The process according to any one of claims 1–8, wherein said sodium donor is employed in an excess of 10–15%.

* * * * *